(12) United States Patent
Wizel et al.

(10) Patent No.: US 7,994,178 B2
(45) Date of Patent: Aug. 9, 2011

(54) CRYSTALLINE ROSUVASTATIN CALCIUM AND COMPOSITIONS THEREOF FOR TREATMENT OF HYPERLIPIDAEMIA

(75) Inventors: Shlomit Wizel, Petah Tiqva (IL); Valerie Niddam-Hildesheim, Kadima (IL); Shalom Shabat, Yavne (IL)

(73) Assignee: Teva Pharmaceutical Industries, Ltd., Petah Tiqva (IL)

( * ) Notice: Subject to any disclaimer, the term of this patent is extended or adjusted under 35 U.S.C. 154(b) by 0 days.

(21) Appl. No.: 11/901,813

(22) Filed: Sep. 18, 2007

(65) Prior Publication Data

US 2008/0176878 A1 Jul. 24, 2008

Related U.S. Application Data

(60) Provisional application No. 60/845,584, filed on Sep. 18, 2006.

(51) Int. Cl.
*A61K 31/4965* (2006.01)
(52) U.S. Cl. .................................. 514/255.06; 544/336
(58) Field of Classification Search ............. 514/255.06; 544/336
See application file for complete search history.

(56) References Cited

U.S. PATENT DOCUMENTS

| | | | |
|---|---|---|---|
| 6,589,959 | B1 | 7/2003 | Taylor |
| 7,129,352 | B2 | 10/2006 | Taylor et al. |
| 2004/0009997 | A1 | 1/2004 | Taylor |
| 2005/0209259 | A1 | 9/2005 | Huang |
| 2006/0258882 | A1 | 11/2006 | Niddam-Hildesheim et al. |
| 2007/0037979 | A1 | 2/2007 | Niddam-Hildesheim et al. |

FOREIGN PATENT DOCUMENTS

| | | |
|---|---|---|
| CN | 1807417 | 7/2006 |
| CN | 1821242 | 8/2006 |
| CN | 1307187 C | 3/2007 |
| EP | 1 816 126 | 8/2007 |
| WO | WO 01/60804 | 8/2001 |
| WO | WO 03/097614 | 11/2003 |
| WO | WO 2005/021511 | 3/2005 |
| WO | WO 2005/023778 | 3/2005 |
| WO | WO 2005/023779 | 3/2005 |
| WO | WO 2005/040134 | 5/2005 |
| WO | WO 2005/077916 | 8/2005 |
| WO | WO 2006/035277 | 4/2006 |
| WO | WO 2006/067456 | 6/2006 |
| WO | WO 2006/079611 | 8/2006 |
| WO | WO 2006/091770 | 8/2006 |
| WO | WO 2006/126035 | 11/2006 |
| WO | WO 2006/136408 | 12/2006 |
| WO | WO 2007/041666 | 4/2007 |
| WO | WO 2007/071357 | 6/2007 |
| WO | WO 2007/125547 | 11/2007 |
| WO | WO 2008/015563 | 2/2008 |
| WO | WO 2008/038132 | 4/2008 |
| WO | WO 2008/044243 | 4/2008 |

OTHER PUBLICATIONS

Japanese Office Action, dated Mar. 1, 2011, from corresponding Japanese Patent Application No. 2008-535810 and English-language translation thereof.
Brittain, "X-Ray Diffraction III: Pharmaceutical Applications of X-Ray Powder Diffraction", Pharmaceutical Technology, Spectroscopy, Elsevier, Amsterdam, NL, vol. 16, 2001, pp. 142-150.
McCrone W C, "Polymorphism",Physics and Chemistry of the Organic Solid State, vol. 2, 1965, pp. 725-767.
Watanabe M et al., "Synthesis and Biological Activity of Methanesulfonamide Pyrimidine- and N-Methanesulfonyl Pyrrole-Substituted 3,5-Dihydroxy-6-heptenoates, a Novel Series of of HMG-CoA Reductase Inhibitors", Bioorganic & Medicinal Chemistry, Elsevier Science Ltd., GB, vol. 5, No. 2, 1997, pp. 437-444.
European Office Action, dated Oct. 6, 2010, from corresponding European Patent Application No. 07 838 458.3.
Caira, Mino R., "Crystalline Polymorphism of Organic Compounds", Topics in Current Chemistry, 1998, pp. 163-208, vol. 198, Department of Chemistry, University of Cape Town, South Africa.
Llinas A. et al., "Polymorph Control: Past, Present and Future", *Drug Discovery Today*, 2008, pp. 198-210, vol. 13, No. 5/6, Elsevier Ltd.
Korean Office Action and translation thereof, dated Jun. 15, 2010, from corresponding Korean Patent Application No. 10-2008-7011735.

*Primary Examiner* — James O Wilson
*Assistant Examiner* — Douglas M Willis
(74) *Attorney, Agent, or Firm* — Kenyon & Kenyon LLP

(57) ABSTRACT

The present invention provides a crystalline form of rosuvastatin calcium characterized by an X-ray powder diffraction pattern having peaks at about 4.7, 19.4 and 22.3° 2θ±0.2° 2θ. The crystalline form of the invention may be further characterized by a DSC thermogram with an endotherm at about 132° C. and another broad endotherm at about 220° C. to about 240° C., and a TGA thermogram showing a weight loss of about of 3 to about 5 percent up to about 100° C. The invention also provides a pharmaceutical composition comprising the crystalline rosuvastatin calcium, or a pharmaceutically acceptable salt thereof, and at least one pharmaceutically acceptable excipient.

22 Claims, 3 Drawing Sheets

CRYSTALLINE ROSUVASTATIN CALCIUM AND COMPOSITIONS THEREOF FOR TREATMENT OF HYPERLIPIDAEMIA

CROSS-REFERENCE TO RELATED APPLICATIONS

This application claims the benefit of U.S. Provisional Application No. 60/845,584, filed Sep. 18, 2006. The contents of which are incorporated herein by reference.

BACKGROUND OF THE INVENTION

1. Field of the Invention

The invention relates to a crystalline rosuvastatin calcium and a process for the preparation thereof.

2. Description of Related Art

Rosuvastatin (monocalcium bis (+) 7-[4-(4-fluorophenyl)-6-isopropyl-2-(N-methyl-N-methylsulfonylaminopyrimidin)-5-yl]-(3R,5S)-dihydroxy-(E)-6-heptenoate) is an HMG-CoA reductase inhibitor, developed by Shionogi for the once daily oral treatment of hyperlipidaemia (Ann Rep, Shionogi, 1996; Direct communications, Shionogi, 8 Feb. 1999 & 25 Feb. 2000). Rosuvastatin calcium is a superstatin, which can lower LDL-cholesterol and triglycerides more effectively than first generation statin drugs. Rosuvastatin calcium has the following chemical formula:

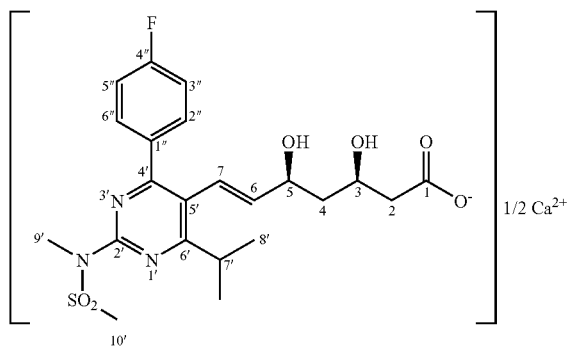

Rosuvastatin calcium is marketed under the name CRESTOR for treatment of a mammal such as a human. According to the maker of CRESTOR, it is administered in a daily dose of from about 5 mg to about 40 mg for LDL cholesterol reduction. For patients requiring less aggressive LDL-C reductions or who have pre-disposing factors for myopathy, a 5 mg dose is recommended, while 10 mg dose is recommended for the average patient, 20 mg dose for patients with marked hypercholesterolemia and aggressive lipid targets (>190 mg/dL), and the 40 mg dose for patients who have not been responsive to lower doses.

Rosuvastatin calcium salt often precipitates as an amorphous material.

U.S. Pat. No. 6,589,959 discloses a crystalline form of rosuvastatain calcium, designated form A. WO 2005/023779 discloses a crystalline hydrated form of rosuvastatin calcium, designated form B, and the dehydrated form, designated form B-1.

The present invention relates to the solid state physical properties of rosuvastatin calcium. Solid state physical properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch, or tribasic calcium phosphate.

Another important solid state property of a pharmaceutical compound is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulating syrups, elixirs and other liquid medicaments. The solid state form of a compound may also affect its behavior on compaction and its storage stability.

These practical physical characteristics are influenced by the conformation and orientation of molecules in the unit cell, which defines a particular polymorphic form of a substance. The polymorphic form may give rise to thermal behavior different from that of the amorphous material or another polymorphic form. Thermal behavior is measured in the laboratory by such techniques as capillary melting point, thermogravimetric analysis (TGA) and differential scanning calorimetric (DSC) and can be used to distinguish some polymorphic forms from others. A particular polymorphic form may also give rise to distinct spectroscopic properties that may be detectable by powder X-ray crystallography, solid state $^{13}C$ NMR spectrometry, and infrared spectrometry.

One of the most important physical properties of a pharmaceutical compound, which can form polymorphs or solvates, is its solubility in aqueous solution, particularly the solubility in gastric juices of a patient. Other important properties relate to the ease of processing the form into pharmaceutical dosages, as the tendency of a powdered or granulated form to flow and the surface properties that determine whether crystals of the form will adhere to each other when compacted into a tablet.

There is a need in the art for new polymorphic forms of rosuvastatin calcium.

BRIEF SUMMARY OF THE INVENTION

In one embodiment, the present invention provides a crystalline form of rosuvastatin calcium characterized by an X-ray powder diffraction pattern having peaks at about 4.7, 19.4 and 22.3° 2θ±0.2° 2θ.

The invention also encompasses a process for preparing a crystalline form of rosuvastatin calcium characterized by X-ray powder diffraction peaks at about 4.7, 19.4 and 22.3° 2θ±0.2° 2θ.

In another embodiment, the invention provides a pharmaceutical composition including the crystalline rosuvastatin calcium of the present invention, or a pharmaceutically acceptable salt thereof, and at least one pharmaceutically acceptable excipient.

In a further embodiment, the invention provides a process for preparing a pharmaceutical formulation including combining crystalline rosuvastatin calcium of the present invention, or a pharmaceutically acceptable salt thereof, with at least one pharmaceutically acceptable excipient.

The invention further provides the use of crystalline rosuvastatin calcium of the present invention, or a pharmaceutically acceptable salt thereof, for the manufacture of a pharmaceutical composition.

The invention also provides a method of treatment including administering a pharmaceutical composition containing the rosuvastatin calcium of the present invention, or prepared from the rosuvastatin calcium of the present invention, to a mammal in need thereof.

DETAILED DESCRIPTION OF THE INVENTION

The discovery of new polymorphic forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic. The invention provides a new polymorphic form of rosuvastatin calcium.

Figure 1:
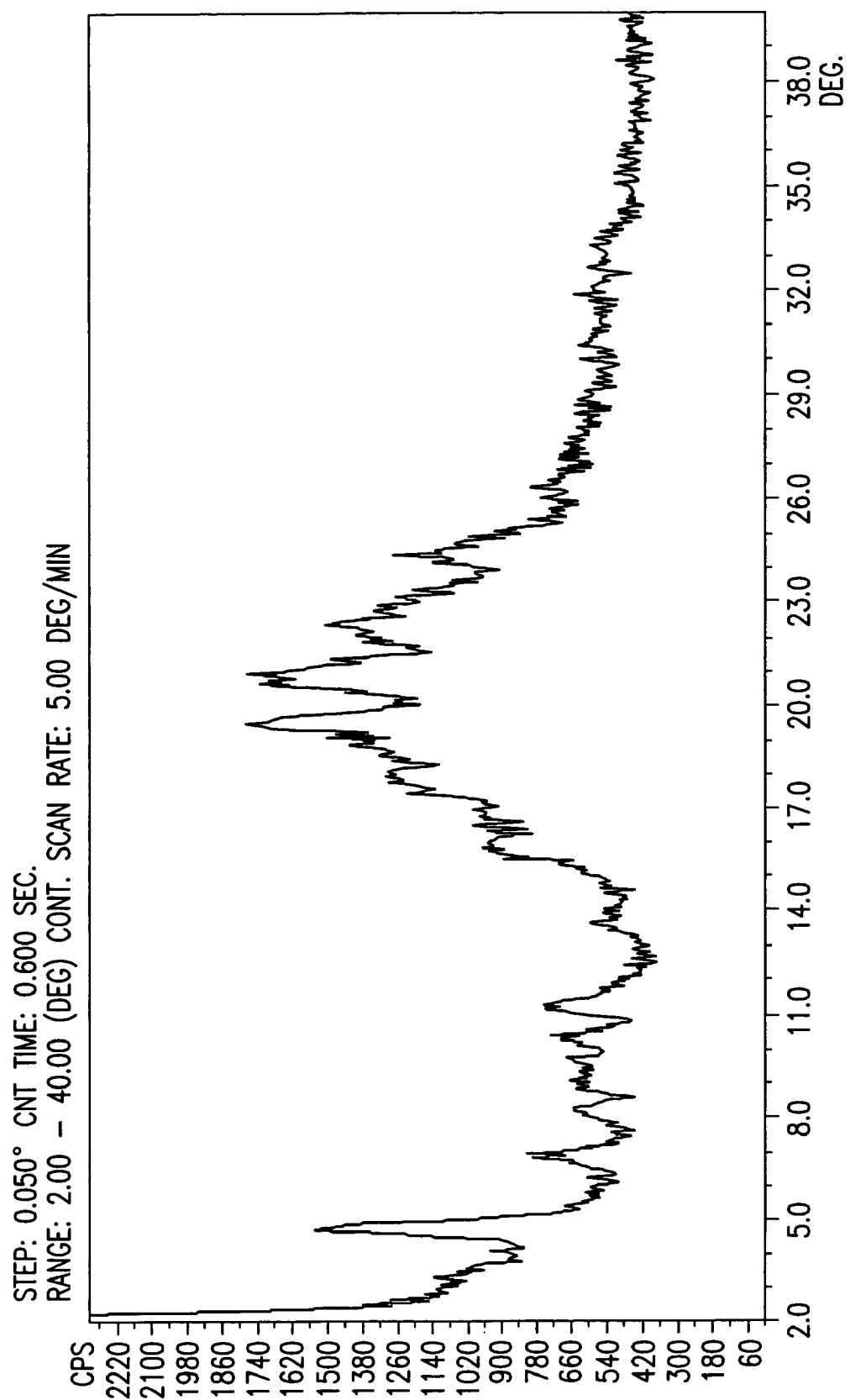
FIG. 1 illustrates a characteristic X-Ray Powder Diffractogram of crystalline rosuvastatin calcium having X-ray powder diffraction peaks at about 4.7, 19.4 and 22.3° 2θ±0.2° 2θ.

The invention encompasses a crystalline form of rosuvastatin calcium characterized by an X-ray powder diffraction pattern having peaks at about 4.7, 19.4 and 22.3° 2θ±0.2° 2θ. The crystalline form may be further characterized by X-ray powder diffraction peaks at about 6.9, 11.1, 15.7, 20.9 and 24.3° 2θ±0.2° 2θ. The crystalline form may also be substantially identified by the PXRD pattern depicted in FIG. 1.

Figure 2:
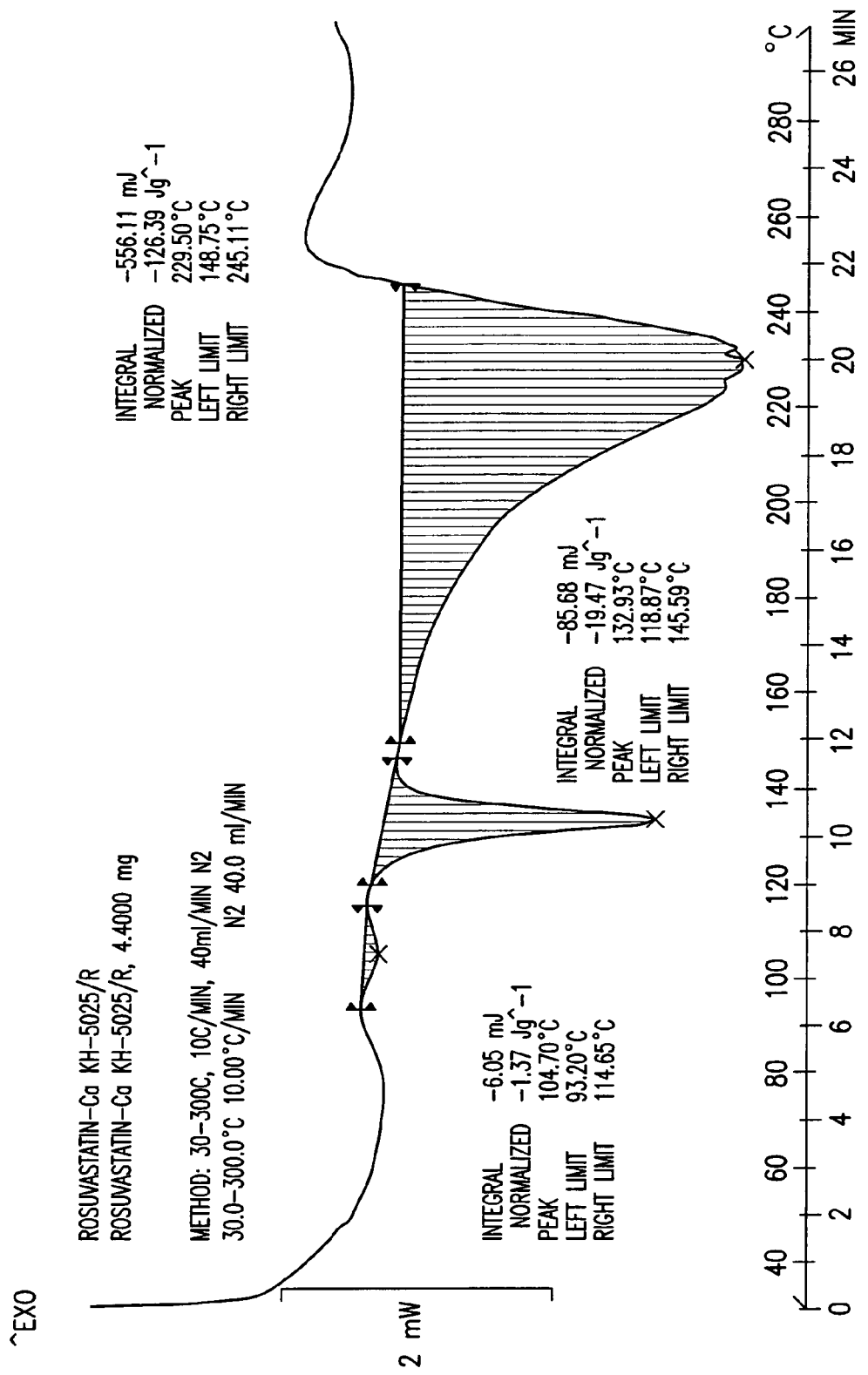
FIG. 2 illustrates a characteristic DSC thermogram of crystalline rosuvastatin calcium having X-ray powder diffraction peaks at about 4.7, 19.4 and 22.3° 2θ±0.2° 2θ.

The crystalline form of the invention may be further characterized by a DSC thermogram with an endotherm at about 132° C. and another broad endotherm at about 220° C. to about 240° C. The crystalline form may also be substantially identified by the DSC curve depicted in FIG. 2.

Figure 3:
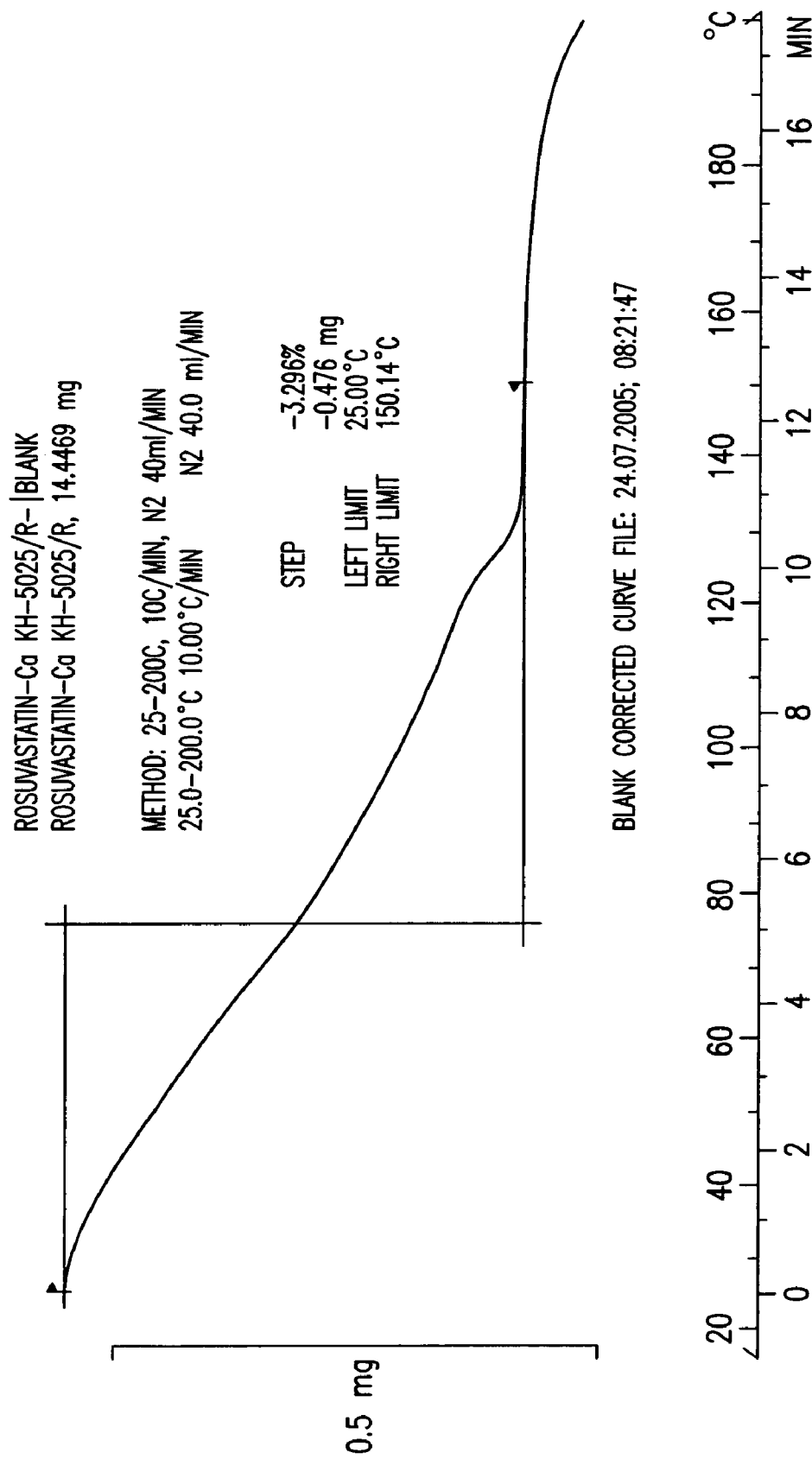
FIG. 3 illustrates a characteristic TGA spectrum of crystalline rosuvastatin calcium having X-ray powder diffraction peaks at about 4.7, 19.4 and 22.3° 2θ±0.2° 2θ.

In addition, the crystalline form may be further characterized by a TGA thermogram showing a weight loss of about of 3 to about 5 percent up to about 100° C. Moreover, the crystalline form may be substantially identified by the TGA curve depicted in FIG. 3. According to Karl-Fisher analysis, the water content of the crystalline rosuvastatin calcium is the same as measured by TGA.

Preferably, the crystalline rosuvastatin calcium is polymorphically pure, i.e., contains no more than about 30% of rosuvastatin calcium form A, more preferably, the crystalline rosuvastatin calcium contains no more than about 20% of rosuvastatin calcium form A, as percentage area XRD. A person skilled in the art can select a characterizing peak or a number of peaks from the known crystalline form and quantify the polymorphic purity according to the European Pharmacopoeia version 5.6, "Characterization of crystalline solids by XRPD", pg 4432-4437."

The invention also encompasses a process for preparing a crystalline form of rosuvastatin calcium characterized by an X-ray powder diffraction pattern having peaks at about 4.7, 19.4 and 22.3° 2θ±0.2° 2θ by slurrying amorphous rosuvastatin calcium in water for more than about 10 hours.

Preferably, the water is in amount of about 2 volumes to about 50 volumes, more preferably, in an amount of about 10 volumes.

Preferably, the slurry is stirred. Preferably, the stirring is at a temperature of about 20° C. to about 40° C., more preferably, at a temperature of about 25° C. Preferably, the stirring is for about 10 to about 48 hours, more preferably, for about 24 hours.

Preferably, the process further includes a cooling step to obtain a precipitate. Preferably, the cooling is to a temperature of about 15° C. to about 0° C., more preferably, to a temperature of about 11° C. to about 5° C.

Preferably, the precipitate upon cooling is filtered and washed to obtain a powder. Preferably, the obtained precipitate is recovered. Preferably, the recovery comprises isolation and washing. Preferably, the isolation is by filtration. Preferably, the washing is with water.

The invention also encompasses a pharmaceutical composition comprising the crystalline rosuvastatin calcium of the present invention, or a pharmaceutically acceptable salt thereof, and at least one pharmaceutically acceptable excipient. Pharmaceutical compositions of the invention contain the crystalline rosuvastatin calcium of the present invention, optionally in mixture with other crystalline forms and/or other active ingredients. In certain embodiments, the pharmaceutical compositions of the invention comprise the crystalline rosuvastatin calcium of the present invention and less than 50%, less than 25%, less than 10%, less than 5%, or less than 1% (by weight of all forms of rosuvastatin calcium present) of other crystalline or amorphous forms of rosuvastatin calcium. In certain embodiments, the pharmaceutical compositions of the invention comprise a therapeutically effective amount of the crystalline rosuvastatin calcium of the present invention.

The invention further encompasses a process for preparing a pharmaceutical formulation comprising combining crystalline rosuvastatin calcium of the present invention, or a pharmaceutically acceptable salt thereof, with at least one pharmaceutically acceptable excipient.

The invention further encompasses the use of crystalline rosuvastatin calcium of the present invention, or a pharmaceutically acceptable salt thereof, for the manufacture of a pharmaceutical composition.

Pharmaceutical compositions of the invention include excipients. Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol and tartaric acid.

Solid and liquid compositions may also be dyed using any pharmaceutically acceptable colorant to improve their appearance and/or facilitate patient identification of the product and unit dosage level.

In liquid pharmaceutical compositions of the invention, rosuvastatin calcium and any other solid excipients are dissolved or suspended in a liquid carrier such as water, vegetable oil, alcohol, polyethylene glycol, propylene glycol or glycerin. Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxyl toluene, butylated hydroxyanisole and ethylenediamine tetraacetic acid may be added at levels safe for ingestion to improve storage stability.

According to the invention, a liquid composition may also contain a buffer such as guconic acid, lactic acid, citric acid or acetic acid, sodium guconate, sodium lactate, sodium citrate or sodium acetate. Selection of excipients and the amounts used may be readily determined by the formulation scientist based upon experience and consideration of standard procedures and reference works in the field.

The solid compositions of the invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges, as well as liquid syrups, suspensions and elixirs. The dosage form of the invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the invention may comprise any of the aforementioned blends and granulates that were described with reference to tableting, however, they are not subjected to a final tableting step. The oral dosage form of the invention is preferably in the form of an oral capsule having a dosage of about 5 mg to about 40 mg, more preferably capsules of 5, 10, 20 and 40 mg.

The invention also encompasses a method of treatment including administering a pharmaceutical composition containing the rosuvastatin calcium of the present invention, or prepared from the rosuvastatin calcium of the present invention, to a mammal in need thereof Solid-State Characterization Crystalline rosuvastatin calcium of the invention was characterized by X-Ray powder diffraction (XRD), DSC analysis and FTIR spectroscopy.

XRD

XRD Diffractograms were collected on Scintag X-Ray powder diffractometer model X'TRA, Cu-tube, solid state detector. Scanning parameters:
Range: 2-40 deg. 2θ: continuous scan, Rate: 3.00 deg./min.

Thermal Analysis

Differential Scanning Calorimetry was performed on DSC821$^e$, Mettler Toledo.
The crucible was crimped and punched prior to analysis.
Experimental Conditions:
Sample weight: 3-5 mg. Heating rate: 10 deg/min.

EXAMPLES

Example 1

Process for the Preparation of Crystalline Form of Rosuvastatin Calcium Characterized by X-Ray Powder Diffraction Peaks at about 4.7, 19.4 and 22.3° 2θ±0.2° 2θ

A 500 ml reactor equipped with a mechanical stirrer was charged with water (150 ml) and amorphous rosuvastatin calcium (10 g). The mixture was stirred at 25±5° C. for 24 hours. The resulting slurry was then cooled to 5-10° C., stirred at this temperature for 1 hr, filtered and washed with water (2×10 ml) to get a powdery compound.

Having thus described the invention with reference to particular preferred embodiments and illustrated it with Examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. All references mentioned herein are incorporated in their entirety.

The invention claimed is:

1. A crystalline form of rosuvastatin calcium characterized by an X-ray powder diffraction pattern with peaks at 4.7, 19.4 and 22.3° 2θ±0.2° 2θ.

2. The crystalline form of claim 1, wherein the crystalline form is further characterized by an X-ray powder diffraction with peaks at 6.9, 11.1, 15.7, 20.9 and 24.3° 2θ±0.2° 2θ.

3. The crystalline form of claim 1, wherein the crystalline form is characterized by the X-ray powder diffraction pattern depicted in FIG. 1.

4. The crystalline form of claim 1, wherein the crystalline form has a differential scanning calorimetry thermogram with an endotherm at about 132° C. and another endotherm at about 220° C. to about 240° C.

5. The crystalline form of claim 1, wherein the crystalline form is characterized by the differential scanning calorimetry curve depicted in FIG. 2.

6. The crystalline form of claim 1, wherein the crystalline form is further characterized by a thermogravimetric analysis thermogram showing a weight loss of about 3 to about 5 percent up to about 100° C.

7. The crystalline form of claim 1, wherein the crystalline form is characterized by the thermogravimetric analysis curve depicted in FIG. 3.

8. The crystalline form of claim 1, wherein the crystalline form contains no more than about 10% of other polymorphic forms of rosuvastatin calcium as percentage area X-ray diffraction.

9. A pharmaceutical composition comprising the crystalline rosuvastatin calcium of claim 1 and at least one pharmaceutically acceptable excipient.

10. A process for preparing the crystalline form of rosuvastatin calcium of claim 1 comprising slurrying amorphous rosuvastatin calcium in water for more than about 10 hours to obtain the crystalline form of rosuvastatin calcium.

11. The process of claim 10, wherein the water is in an amount of about 2 volumes to about 50 volumes.

12. The process of claim 10, wherein the slurry is stirred.

13. The process of claim 10, wherein the slurry is stirred for about 10 to about 48 hours.

14. The process of claim 10, wherein the slurry is at a temperature of about 20° C. to about 40° C.

15. The process of claim 10, wherein the slurry is at a temperature of about 25° C.

16. The process of claim 10, wherein the slurry is further cooled to a temperature of about 15° C. to about 0° C.

17. The process of claim 16, wherein the slurry is cooled to a temperature of about 10° C. to about 5° C.

18. The process of claim 10, wherein the obtained crystalline form of rosuvastatin calcium is recovered.

19. The process of claim 18, wherein the recovery comprises isolation and washing.

20. The process of claim 19, wherein the isolation is by filtration.

21. The process of claim 19, wherein the washing is with water.

22. A method of lowering cholesterol in a mammal comprising administering the pharmaceutical composition of claim 9 to the mammal.

* * * * *

UNITED STATES PATENT AND TRADEMARK OFFICE
CERTIFICATE OF CORRECTION

PATENT NO.         : 7,994,178 B2                                                    Page 1 of 1
APPLICATION NO.    : 11/901813
DATED              : August 9, 2011
INVENTOR(S)        : Shlomit Wizel, Valerie Niddam-Hildesheim and Shalom Shabat It is certified that error appears in the above-identified patent and that said Letters Patent is hereby corrected as shown below:

On the Title Page, item (57), Abstract, change the first three occurrence of "C." to -- C --.

At column 3, line 67, change each occurrence of "C." to -- C --.

At column 4, line 6, change each occurrence of "C." to -- C --.

At column 4, line 7, change the first occurrence of "C." to -- C --.

At column 7, line 30, change "C." to -- C --.

At column 7, line 31, change "C." to -- C --.

At column 8, line 3, change "C." to -- C --.

At column 8, line 4, change the first occurrence of "C." to -- C --.

At column 8, line 33, change the first occurrence of "C." to -- C --.

At column 8, line 37, change the first occurrence of "C." to -- C --.

At column 8, line 39, change the first occurrence of "C." to -- C --.

Signed and Sealed this
Eleventh Day of October, 2011

David J. Kappos
*Director of the United States Patent and Trademark Office*